Feb. 25, 1941. J. H. NICOLAS Plant Pat. 457
ROSE PLANT
Filed Oct. 23, 1940
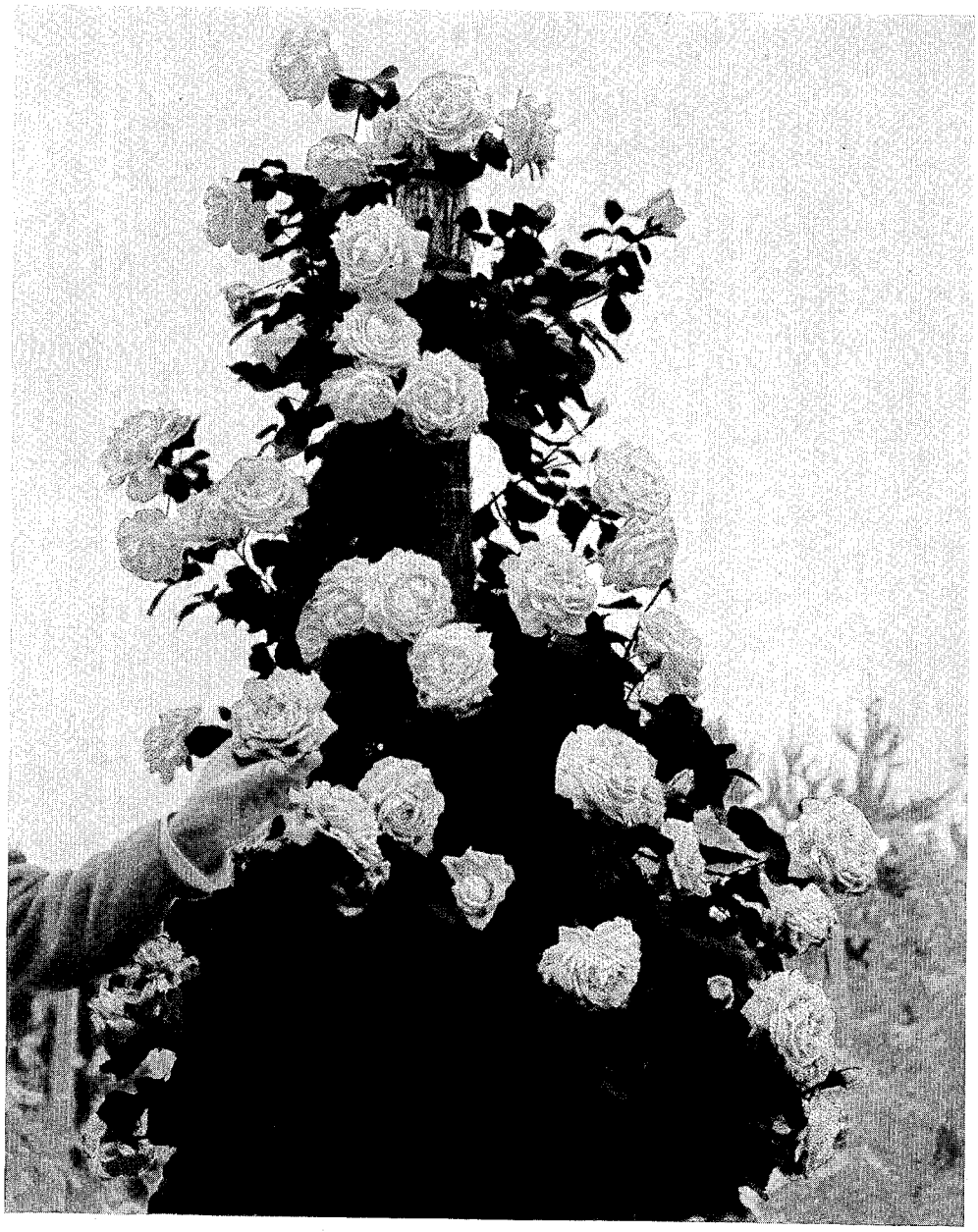
Inventor
Jean H. Nicolas
By Fannie Nicolas
Administratrix of the estate
of Jean H. Nicolas, deceased.
By Robb & Robb
attorneys Patented Feb. 25, 1941

Plant Pat. 457

UNITED STATES PATENT OFFICE

457

ROSE PLANT

Jean H. Nicolas, deceased, late of Newark, N. Y., by Fannie Nicolas, administratrix, Newark, N. Y., assignor to Jackson & Perkins Company, Newark, N. Y.

Application October 23, 1940, Serial No. 362,470

1 Claim. (Cl. 47—61)

The present invention relates to a new and distinct variety of hybrid climbing rose plant, the result of a definite effort to produce an improved rose of the pillar type.

From the cross of an unknown seedling and the known variety Georg Arends, this novel rose was produced having the important characteristics of continuous remontance, new flowering shoots appearing immediately, under the blooms as soon as flowers are matured; full petaled flowers on a hardy pillar rose; the novel coloring of the flowers not previously found in hardy pillar roses of deep rose to thulite pink color; the large size of flowers and extreme hardiness of the plant in northern New York when given only average protection.

By a sexual reproduction these characteristics have been found to be established.

Other features of novelty are set forth in the following detail description of this new variety in which the color terminology is in accord with Ridgway's Color Standard.

Parentage:

*Seed parent.*—Unknown seedling.

*Pollen parent.*—Georg Arends.

Classification:

*Botanic.*—Hybrid climber.

*Commercial.*—Everblooming pillar.

*Flower*

Observations made at Newark, New York, in the morning of October 2, 1940.

Blooming habit: Recurrent—continuous.

Bud:

*Size.*—Medium.

*Form.*—Ovoid. Is not affected by wet or hot weather.

*Color.*—When sepals first divide—Spinel Red, Plate 26. When petals begin to unfurl—Deep Rose Pink, Plate 12. When half blown: inside of petals—Deep Rose Pink, Plate 12, lightening to Rose Pink, Plate 12, at the base; reverse of petals—edges Rose Pink, Plate 12, center Cameo Pink, Plate 26.

*Sepals.*—Serrated, slightly branched. Curl back when petals begin to unfurl. *Color*: outside—Light Cress Green, Plate 31, inside—Absinthe Green, Plate 31.

*Calyx.*—*Shape*—funnel. *Size*—large. *Aspect*—smooth. *Color*—Light Cress Green, Plate 31.

*Peduncle.* — *Length* — medium. *Aspect* — smooth. *Color*—Yellowish Oil Green, Plate 5. *Strength*—stiff; heavy.

*Opening.*—Bud opens well. Is not affected by adverse conditions.

Bloom:

*Size.*—Large. Average size when fully expanded—4½ to 5 inches.

*Borne.*—In clusters, irregular.

*Stems.*—Long; strong.

*Form.*—When first open—globular. *Permanence*—retains its form to the end; outer petals curl back; balance of flowers keep form.

*Petalage.*—Very double (many petals and stamens hidden). Number of petals under normal conditions—50 to 55.

*Color.*—Center of flower—between Deep Rose, Plate 12, and Thulite Pink, Plate 26. Outer petals—Rose Pink, Plate 12. Base of petals (aiglet)—Picric Yellow, Plate 4. Inside of petals—Rose Pink, Plate 12, lightening to Cameo Pink, Plate 26, at base of petal. Reverse of petals—edges Rosolane Pink, Plate 26, with Cameo Pink, Plate 26, flushing through the White, Plate 53, in center.

*Discoloration.*—General tonality at end of first day—Thulite Pink, Plate 26. Second day—Thulite Pink, Plate 26. Third day—upper edges Rose Pink, Plate 12, with interior Thulite Pink, Plate 26.

Petals:

*Texture.*—Leathery. Is not affected by wet or hot weather.

*Appearance.*—Inside—velvety. Outside—shiny.

*Form.*—Oval, pointed.

*Arrangement.*—Imbricated (regularly arranged shinglelike). *Petaloids in center*—few.

*Persistence.*—Drop off cleanly.

*Fragrance.*—Strong. *Nature*—"Old Rose perfume" (Centifolia).

*Lasting Quality.*—On the plant and as cut flower—long.

Genital organs:

*Stamens, anthers.*—Medium size; many. *Color*—Light Cadmium, Plate 4. *Arrangement*—regular around styles.

*Stamens, filaments (threads).*—Medium length. *Color*—Pale Lemon Yellow, Plate 4.

*Pollen.*—Martius Yellow, Plate 4.

*Styles.*—Bunched, uneven length; medium length; thin.

*Stigmas.*—Picric Yellow, Plate 4.

*Ovaries.*—All enclosed in calyx.

*Plant*

Form: Pillar.

Growth: Vigorous; upright.

Foliage: 5 to 7 leaflets.

*Size.*—Large.

*Quantity.*—Abundant.

*Color.—New foliage:*—upper side—edges Vandyke Red, Plate 13, center Yellowish Oil Green, Plate 5; under side—Vandyke Red, Plate 13, and veined Yellowish Oil Green, Plate 5. *Old foliage:*—upper side—Dark Cress Green, Plate 31; under side—Cress Green, Plate 31. *Shape*—oval pointed. *Texture:*—upper side—leathery; under side—rough. *Ribs and veins*—prominent.

*Edge.*—Serrated (saw toothed).

*Serration.*—Single; small.

*Rachis.—Color:*—upper side—Dark Cress Green, Plate 31; lower side—Cress Green, Plate 31; Under side—smooth.

*Stipules.*—Medium length; serrated.

*Disease resistance.*—Resistant.

Wood:

*New wood.—Color*—Biscay Green, Plate 17, overlaid with Pompeian Red, Plate 13. *Bark*—rough.

*Old wood.—Color*—Cress Green, Plate 31. *Bark*—smooth.

Thorns: (thorns are divided into thorns, prickles, and short needles):

*Thorns.—Quantity*—on main stalks from base and on laterals from stalk—ordinary. *Form*—broad base; short; straight. *Color when young*—Acajou Red, Plate 13. *Position*—irregular.

*Prickles.—Quantity*—on main stalks and on laterals—many. *Color*—Acajou Red, Plate 13.

What is claimed is:

A new and distinct variety of large flowered pillar rose plant, characterized as to novelty by its extreme hardiness, its continuous remontance bearing large deep rose to thulite pink colored flowers, of numerous petals and extremely rich fragrance not previously found in a hardy pillar type rose.

FANNIE NICOLAS,

*Administratrix of the Estate of Jean H. Nicolas, Deceased.*